(12) United States Patent
Lee et al.

(10) Patent No.: US 9,095,329 B2
(45) Date of Patent: Aug. 4, 2015

(54) ELECTROMAGNETIC THERMOTHERAPEUTIC APPARATUS

(75) Inventors: Gwo-Bin Lee, Tainan (TW); Xi-Zhang Lin, Tainan (TW); Sheng-Chieh Huang, Tainan (TW); Yi-Yuan Chang, Donggang Township (TW); Yan-Shen Shan, Tainan (TW); Sheng-Jye Hwang, Tainan (TW); Tung-Jen Lee, Fangyuan Township (TW); Szu-Yin Chen, Tainan (TW); Ping-Hen Chen, Taichung (TW)

(73) Assignee: National Cheng Kung University, Tainan (TW)

( * ) Notice: Subject to any disclaimer, the term of this patent is extended or adjusted under 35 U.S.C. 154(b) by 807 days.

(21) Appl. No.: 13/358,824

(22) Filed: Jan. 26, 2012

(65) Prior Publication Data

US 2012/0209053 A1 Aug. 16, 2012

(30) Foreign Application Priority Data

Feb. 15, 2011 (CN) .......................... 2011 1 0039233

(51) Int. Cl.
*A61B 18/04* (2006.01)
*A61B 18/00* (2006.01)
(52) U.S. Cl.
CPC ....... *A61B 18/04* (2013.01); *A61B 2018/00589* (2013.01)
(58) Field of Classification Search
CPC .................. A61B 18/1477; A61B 2018/00791
USPC ............ 606/41, 44; 604/264, 272; 600/10, 12
See application file for complete search history.

(56) References Cited

U.S. PATENT DOCUMENTS

| 5,702,359 | A | * | 12/1997 | Hofmann et al. | 604/20 |
|---|---|---|---|---|---|
| 5,993,434 | A | * | 11/1999 | Dev et al. | 604/501 |
| 6,277,116 | B1 | * | 8/2001 | Utely et al. | 606/42 |
| 6,918,907 | B2 | * | 7/2005 | Kelly et al. | 606/41 |
| 7,824,394 | B2 | * | 11/2010 | Manstein | 606/9 |
| 2008/0045879 | A1 | * | 2/2008 | Prausnitz et al. | 604/20 |
| 2008/0091182 | A1 | * | 4/2008 | Mehta | 606/29 |
| 2008/0091183 | A1 | * | 4/2008 | Knopp et al. | 606/31 |
| 2010/0152763 | A1 | * | 6/2010 | Kim et al. | 606/189 |
| 2010/0249770 | A1 | * | 9/2010 | Lee et al. | 606/33 |
| 2010/0312237 | A1 | * | 12/2010 | Habib et al. | 606/33 |
| 2011/0004206 | A1 | * | 1/2011 | Habib et al. | 606/33 |
| 2011/0054455 | A1 | * | 3/2011 | Lee et al. | 606/28 |
| 2011/0092884 | A1 | * | 4/2011 | Kang | 604/21 |
| 2011/0258781 | A1 | * | 10/2011 | Kawasaki et al. | 5/652.1 |
| 2012/0259311 | A1 | * | 10/2012 | Hirshberg | 604/506 |
| 2012/0296280 | A1 | * | 11/2012 | Eum | 604/113 |
| 2013/0144257 | A1 | * | 6/2013 | Ross | 604/506 |
| 2014/0303613 | A1 | * | 10/2014 | Azure et al. | 606/34 |

\* cited by examiner

*Primary Examiner* — Joseph Stoklosa
*Assistant Examiner* — Jocelyn D Ram
(74) *Attorney, Agent, or Firm* — Muncy, Geissler, Olds & Lowe, P.C.

(57) ABSTRACT

An electromagnetic thermotherapeutic apparatus includes: a plurality of needle units respectively having head portions and needle portions; a base unit having a base plate that is formed with a plurality of first through holes, and a base pad that is formed with a plurality of second through holes, the needle portions of the needle units removably extending through the second and first through holes, the head portions of the needle units abutting against the base pad; a temperature monitor disposed between the base plate and the base pad; an upper unit disposed above the base pad and abutting against the head portions; and a clamp unit clamping and pressing the base unit against the upper unit.

9 Claims, 4 Drawing Sheets

ELECTROMAGNETIC THERMOTHERAPEUTIC APPARATUS

CROSS-REFERENCE TO RELATED APPLICATION

This application claims priority of Chinese Patent application no. 201110039233.9, filed on Feb. 15, 2011.

BACKGROUND OF THE INVENTION

1. Field of the Invention

This invention relates to a therapeutic apparatus, more particularly to an electromagnetic thermotherapeutic apparatus.

2. Description of the Related Art

Conventional methods of treating hemorrhage are generally classified into physical or chemical methods. In the physical method, damaged blood vessels are ligated or obstructed using surgical techniques. In the chemical method, chemical hemostatic materials are directly applied to the damaged blood vessels. However, the physical method is usually time-consuming and may result in tissue damage, necrosis or other complications, and the chemical hemostatic materials used in the chemical method are unlikely to perfectly attach and cover the damaged blood vessels due to severe bleeding, thereby resulting in inefficient hemostasis effect.

SUMMARY OF THE INVENTION

Therefore, the object of the present invention is to provide an electromagnetic thermotherapeutic apparatus that can provide an efficient treatment for hemorrhage.

An electromagnetic thermotherapeutic apparatus according to the present invention comprises: a plurality of needle units respectively having head portions and needle portions; a base unit having a base plate that is formed with a plurality of first through holes, and a base pad that is disposed on top of the base plate and that is formed with a plurality of second through holes, the needle portions of the needle units removably extending through the second and first through holes, the head portions of the needle units abutting against the base pad; a temperature monitor disposed between the base plate and the base pad to detect the temperature of the base plate; an upper unit disposed above the base pad and abutting against the head portions of the needle units; and a clamp unit clamping and pressing the base unit against the upper unit.

BRIEF DESCRIPTION OF THE DRAWINGS

Other features and advantages of the present invention will become apparent in the following detailed description of the preferred embodiment of this invention, with reference to the accompanying drawings, in which.

DETAILED DESCRIPTION OF THE PREFERRED EMBODIMENT

Figure 1:
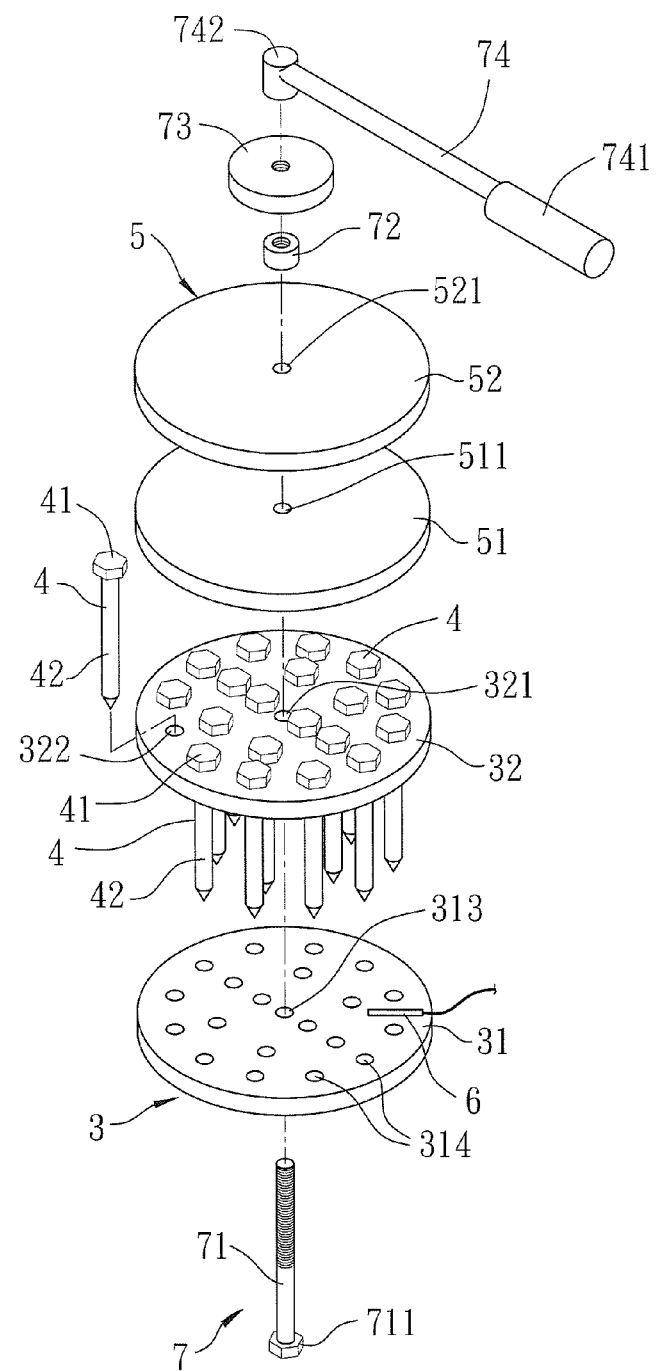
FIG. 1 is an exploded perspective view of the preferred embodiment of an electromagnetic thermotherapeutic apparatus according to this invention.
Figure 2:
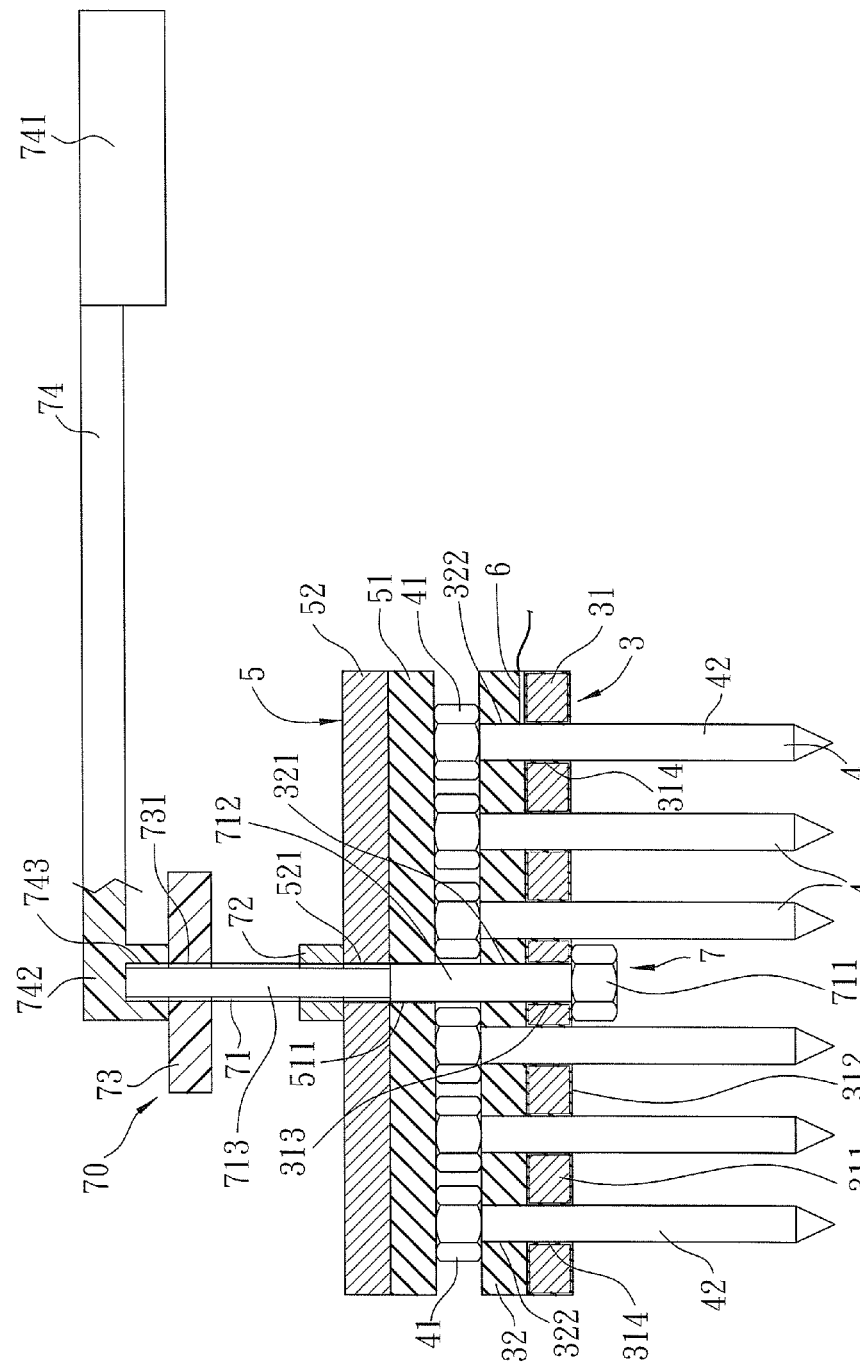
FIG. 2 is a partly schematic sectional view of the preferred embodiment shown in FIG. 1.

FIGS. 1 and 2 show the preferred embodiment of an electromagnetic thermotherapeutic apparatus according to the present invention. The electromagnetic thermotherapeutic apparatus comprises a base unit 3, a plurality of needle units 4, an upper unit 5, a temperature monitor 6, and a clamp unit 7.

Figure 3:
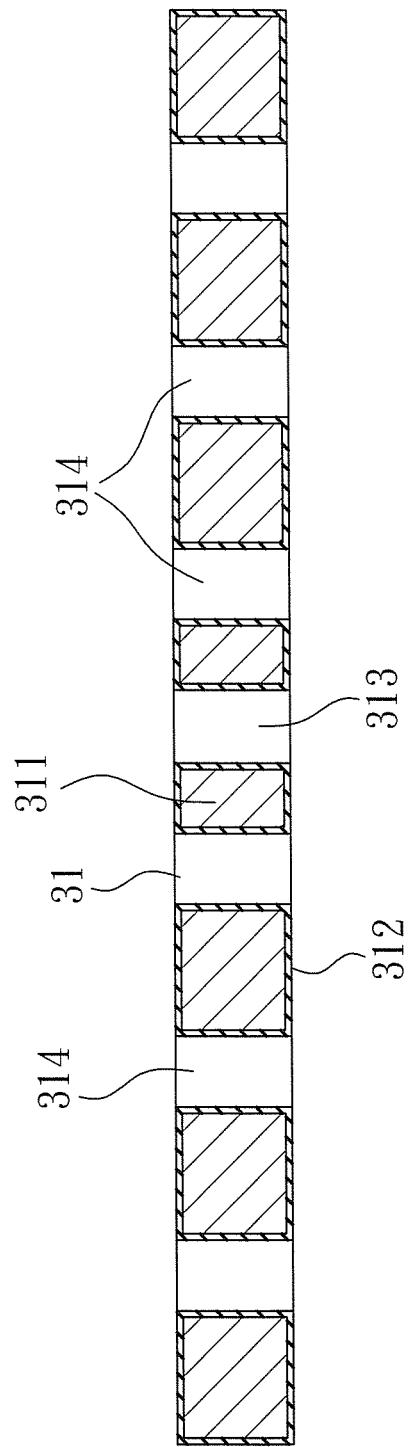
FIG. 3 is a schematic sectional view illustrating a base plate of the preferred embodiment shown in FIG. 1.

The base unit 3 has a base plate 31 and a base pad 32 that is disposed on top of the base plate 31. Referring to FIG. 3, the base plate 31 has a plurality of electromagnetic inductive parts 311, a plurality of non-electromagnetic inductive parts 312 each of which completely encloses a respective one of the electromagnetic inductive parts 311, a first axle hole 313, and a plurality of first through holes 314. Each of the electromagnetic inductive parts 311 is made of an electromagnetic inductive material that is capable of generating heat when subjected to an induction magnetic field and that has high temperature resistance.

The base pad 32 is made from a non-electromagnetic inductive material with high temperature resistance and low-hardness, such as, Teflon and silicon rubber. The base pad 32 has a second axle hole 321 corresponding to the first axle hole 313 of the base plate 31, and a plurality of second through holes 322 formed corresponding to the first through holes 314 of the base plate 31.

Figure 4:
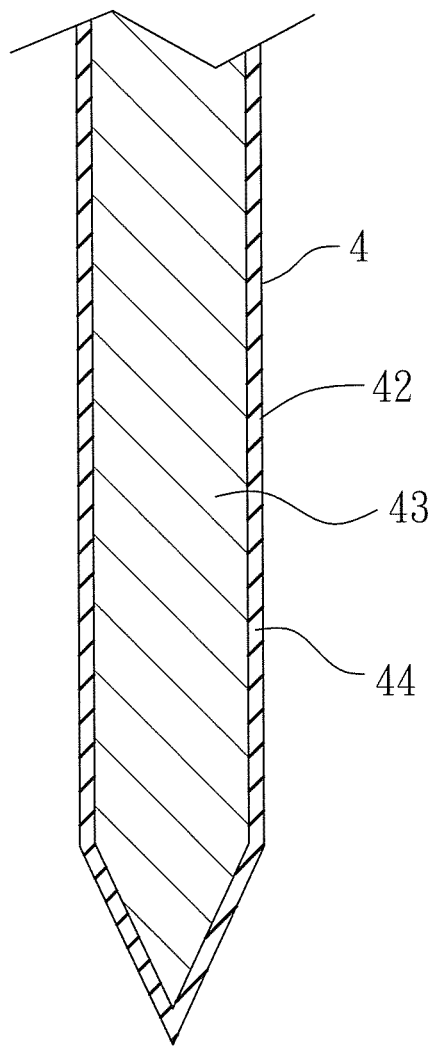
FIG. 4 is a fragmentary sectional view illustrating a needle portion of a needle unit of the preferred embodiment shown in FIG. 1.

Each of the needle units 4 has a head portion 41 that abuts against a top side of the base pad 32, and a needle portion 42 that removably extends downwardly through the second and first through holes 322, 314, and that is partially exposed from the base unit 3. Referring to FIG. 4, the needle portion 42 of each of the needle units 4 includes an electromagnetic inductive core part 43 that is made of an electromagnetic inductive material capable of generating heat when subjected to an induction magnetic field, and a protective shell 44 that encloses the electromagnetic inductive core part 43.

In this embodiment, the electromagnetic inductive part 311 and the electromagnetic inductive core part 43 are made from stainless steel. The electromagnetic inductive part 311 and the electromagnetic inductive core part 43 may be made from iron or other electromagnetic inductive materials. The non-electromagnetic inductive part 312 and the protective shell 44 are made from a non-electromagnetic inductive material with high temperature resistance, such as, Teflon and ceramics, and are utilized to prevent oxidation of the electromagnetic inductive part 311 and the electromagnetic inductive core part 43, respectively, and prevent sticking of human tissue and body fluid on the electromagnetic inductive part 311 and the electromagnetic inductive core part 43.

The temperature monitor 6 is disposed between the base plate 31 and the base pad 32. The temperature monitor 6 is electrically connected to the electromagnetic thermotherapeutic apparatus of this invention, and is used for detecting the temperature of the base plate 31. In this embodiment, the temperature monitor 6 is a thermo-electric couple.

The upper unit 5 is disposed above the base pad 32, and includes an upper pad 51 that abuts against the head portions 41 of the needle units 4, and an upper plate 52 that is disposed above the upper pad 51. The upper pad 51 has a third axle hole 511 corresponding to the second axle hole 321 of the base pad 32, and is made from a material the same as that of the base pad 32. The upper plate 52 has a fourth axle hole 521 corresponding to the third axle hole 511 of the upper pad 51, and can be made of an electromagnetic inductive material or a non-electromagnetic inductive material. In this embodiment, the upper plate 52 is made of an electromagnetic inductive material. It should be noted that, in this invention, the upper pad 51 is optional and can be dispensed with.

The clamp unit 7 includes a nut 72, and a bolt 71 that has a bolt head 711 and a bolt rod 712. The bolt head 711 abuts against a bottom side of the base plate 31. The bolt rod 712 extends upwardly through the first, second, third and fourth axle holes 313, 321, 511, 521, such that an exposed portion 713 of the bolt rod 712 is exposed from the upper plate 52. The nut 72 is disposed above the upper plate 52, and is threadedly attached to the exposed portion 713 of the bolt rod 712. The nut 72 abuts against a top side of the upper plate 52 so as to clamp and press the base unit 3 against the upper unit 5 with the bolt 71.

The electromagnetic thermotherapeutic apparatus of this invention further comprises a handling unit 70 that is removably attached to the exposed portion 713 of the bolt rod 712 above the nut 72. In this embodiment, the handling unit 70 includes a circular handling plate 73 that has a threaded through hole 731 threadedly engaging the exposed portion 713 of the bolt rod 712, and a handling bar 74 that has a handling part 741 and a socket part 742 connected to the handling part 741 and connected threadedly to the bolt 71 above the nut 72. Specifically, the handling bar 74 has a threaded blind hole 743 threadedly engaging the exposed portion 713 of the bolt rod 712. The handling plate 73 and the handling bar 74 are made of a non-electromagnetic inductive material with high temperature resistance, and are intended to be held by hand or other fixtures. By virtue of the handling plate 73 and the handling bar 74, the electromagnetic thermotherapeutic apparatus can be stably positioned, i.e., the base plate 31 can stably abut a surface of damaged tissues or organs and the needle units 4 can be precisely inserted into the damaged tissues or organs to treat hemorrhage. Meanwhile, the electromagnetic thermotherapeutic apparatus can be easily removed when the treatment is finished.

In use, the needle portions 42 of the needle units 4 are inserted into a portion of the damaged tissues or organs to be treated, and the base plate 31 stably abuts the surface of the damaged tissues or organs. Subsequently, the needle units 4 and the base plate 31 are heated by induction magnetic field generated by an electromagnetic device. The portion of the damaged tissues or organs to be treated is cauterized so as to achieve hemostasis. The temperature of the base plate 31 of the electromagnetic thermotherapeutic apparatus is detected by the temperature monitor 6, and the data of the measured temperature is transferred to the electromagnetic device and used as a reference to adjust the induction magnetic field to be generated by the electromagnetic device.

Particularly, because of the non-electromagnetic inductive part 312 and the protective shell 44, the sticking of human tissue and body fluid on the base plate 31 and the needle units 4 can be prevented.

In this embodiment, the base and upper units 3, 5 are formed to have circular shapes. However, it should be noted herein that the size and the shape of the base and upper units 3, 5 could vary based on the actual requirements such as the size or shape of the damaged tissues or organs to be treated. For example, the base and upper units 3, 5 may be formed to have square, rectangular or other shapes. The numbers of the needle units 4 also could vary in accordance with the size and the shape of the damaged tissues or organs to be treated.

According to the present invention, the head portions 41 of the needle units 4 are clamped between the base unit 3 and the upper unit 5 so as to improve the stability of the needle units 4 and prevent swinging and loosening of the needle units 4. Moreover, by varying the thickness of the base pad 32, the length of the needle portion 42 exposed from the base plate 31 can be modified. Since the shape and size of the base unit 3, the number of the needle units 4, and the length of the needle portions 42 exposed from the base plate 31 can be adjusted, damage to healthy tissues or organs could be minimized.

While the present invention has been described in connection with what is considered the most practical and preferred embodiment, it is understood that this invention is not limited to the disclosed embodiment but is intended to cover various arrangements included within the spirit and scope of the broadest interpretation and equivalent arrangements.

What is claimed is:

1. An electromagnetic thermotherapeutic apparatus comprising:
   a plurality of needle units respectively having head portions and needle portions;
   a base unit having a base plate that is formed with a plurality of first through holes, and a base pad that is disposed on top of said base plate and that is formed with a plurality of second through holes, said needle portions of said needle units removably extending through said second and first through holes, said head portions of said needle units abutting against said base pad;
   a temperature monitor disposed between said base plate and said base pad to detect the temperature of said base plate;
   an upper unit disposed above said base pad and abutting against said head portions of said needle units; and
   a clamp unit clamping and pressing said base unit against said upper unit.

2. The electromagnetic thermotherapeutic apparatus as claimed in claim 1, wherein said clamp unit includes a bolt penetrating through said base and upper units, and having a bolt head abutting against said base plate, and a nut threadedly attached to said bolt and abutting against said upper unit.

3. The electromagnetic thermotherapeutic apparatus as claimed in claim 2, further comprising a handling unit removably attached to said bolt above said nut.

4. The electromagnetic thermotherapeutic apparatus as claimed in claim 3, wherein said handling unit includes a handling plate connected to said bolt above said nut.

5. The electromagnetic thermotherapeutic apparatus as claimed in claim 3, wherein said handling unit includes a handling bar that has a socket part connected to said bolt above said nut.

6. The electromagnetic thermotherapeutic apparatus as claimed in claim 1, wherein said upper unit includes an upper plate and an upper pad disposed between said head portions of said needle units and said upper plate, said upper pad abutting against said head portions of said needle units.

7. The electromagnetic thermotherapeutic apparatus as claimed in claim 6, wherein said base pad and said upper pad are made of a material which is not electromagnetic-inductive.

8. The electromagnetic thermotherapeutic apparatus as claimed in claim 6, wherein said upper plate is made of an electromagnetic inductive material.

9. The electromagnetic thermotherapeutic apparatus as claimed in claim 1, wherein said needle portion of each of said needle units includes an electromagnetic inductive core part that is made of an electromagnetic inductive material capable of generating heat when subjected to an induction magnetic field, and a protective shell that encloses said electromagnetic inductive core part and that is made of a material which is not electromagnetic-inductive.

* * * * *